United States Patent [19]

Zähner et al.

[11] Patent Number: 5,874,262

[45] Date of Patent: Feb. 23, 1999

[54] MICROBIOLOGICAL PROCESS FOR THE PREPARATION OF (S,S)-N,N'-ETHYLENEDIAMINEDISUCCINIC ACID

[75] Inventors: Hans Zähner, Bern, Switzerland; Ingeborg Cebulla, Schönaich; Michael Harder, Seeheim, both of Germany

[73] Assignee: Ciba Specialty Chemicals Corporation, Tarrytown, N.Y.

[21] Appl. No.: 952,274

[22] PCT Filed: May 4, 1996

[86] PCT No.: PCT/EP96/01868

§ 371 Date: Jan. 23, 1998

§ 102(e) Date: Jan. 23, 1998

[87] PCT Pub. No.: WO96/36725

PCT Pub. Date: Nov. 21, 1996

[30] Foreign Application Priority Data

May 17, 1995 [DE] Germany ................ 19518150

[51] Int. Cl.⁶ ..................................... C12P 13/00
[52] U.S. Cl. ............... 435/128; 435/280; 435/252.1; 435/822
[58] Field of Search .................... 435/128, 280, 435/252.1, 822

[56] References Cited

U.S. PATENT DOCUMENTS 5,707,836  1/1998  Endo et al. ................ 435/109

FOREIGN PATENT DOCUMENTS 2082023  5/1993  Canada .
0540975  5/1993  European Pat. Off. .

OTHER PUBLICATIONS

APS JPOABS 08–301824 Yamamoto et al. "Production of Biodegradable Chelating Agent as L,L–ethylenediamine-disuccinic Acid and its Alkali Metallic Salt Through Schiff Base of Glyoxal", Nov. 19, 1996.

ATCC "Catalogue of Bacteria & Bacteriophages" 18th Edition 1992 p. 26 Amycolatoopsis Orientalis Ed. Gherna et al.

The Journal of Antibiotics, Apr. 1984, p. 426 Biotechabs, ref. #84–06633.

*Primary Examiner*—Herbert J. Lilling
*Attorney, Agent, or Firm*—Kevin T. Mansfield

[57] ABSTRACT

A microbiological process for the preparation of N,N'-ethylenediaminedisuccinic acid of formula (1), by (a) pre-cultivation of a strain of the genus *Amycolatopsis orientalis* on a specified nutrient medium (1st preculture), (b) inoculation of a nutrient solution of the same composition as the base of the production fermenter by the 1st preculture (2nd preculture), (c) inoculation of the base nutrient solution in the production fermenter with the 2nd preculture and incubation in accordance with a specified timetable, (d) feeding of the production fermenter in the fed-batch process with a feeding solution under aerobic conditions at a pH of from 2 to 8 and at a temperature of from 15° to 40° C., wherein the base nutrient and feeding solutions are free of zinc-containing compounds, is described. The compound prepared by the process according to the invention is suitable as complexing agent with good biodegradability in detergents.

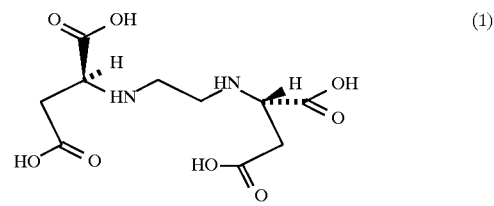

(1)

5 Claims, No Drawings

MICROBIOLOGICAL PROCESS FOR THE PREPARATION OF (S,S)-N,N'-ETHYLENEDIAMINEDISUCCINIC ACID

The present invention relates to a microbiological process for the preparation of (S,S)-N,N'-ethylenediaminedisuccinic acid (abbreviated to "EDDS" hereinafter).

Ethylenediaminetetraacetic acid (EDTA) and nitrilotriacetic acid (NTA) are used on a large scale as complexing agents in household detergents. However, these known complexing agents have very low biodegradability and are not retained in the usual biological treatment of waste water. It is known that the (S,S) configuration of EDDS has good properties as a complexing agent and, at the same time, is biodegradable. This compound could therefore be used as an alternative to EDTA and NTA, provided that this complexing agent can be prepared in a cost-effective process.

EDDS has two asymmetric carbon atoms. Various stereoisomeric forms of the compound are therefore possible. The (S,S) configuration of EDDS corresponds to the formula

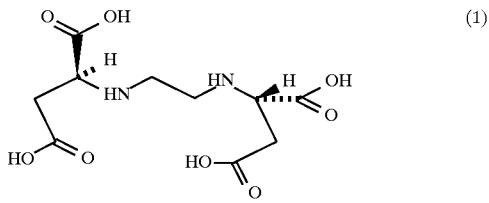

(1)

A cost-effective chemical synthesis leads to a mixture of the three forms S,S; R,R; and meso-EDDS. However, separation of these stereoisomeric compounds requires great industrial complexity. The direct routes disclosed to date for synthesising (S,S)-EDDS are based on starting materials which do not per se permit the product to be justified in terms of cost.

T. Nishikiori et al. have found an actinomyces strain which is able to produce optically pure (S,S)-EDDS (T. Nishikiori et al., Production by Actinomycetes of (S,S)-N, N'-ethylenediaminedisuccinic acid, an inhibitor of phospholipase c; J.Antibiotics 37, 426–427 (1984)). (S,S)-EDDS was isolated from an actinomyces strain (MG 417-CF 17) in the search for inhibitors of phospholipase C. On cultivation of the strain on a complex nutrient medium comprising 1.5% cottonseed meal, 1.5% glycerol, 2% L-asparagine and 0.3% sodium chloride, however, only low yields of 170 mg/l EDDS were obtained. In addition, the isolation is very elaborate and requires several stages.

The object of the present invention is therefore to provide a simple and cost-effective microbiological process for the preparation of optically pure (S,S)-EDDS.

It has now been found, surprisingly, that the yield of (S,S)-EDDS can be increased, and the work up can be considerably simplified, when certain optimised fermentation conditions are observed in a microbiological preparation process.

The present invention therefore relates to a microbiological process for the preparation of N,N'-ethylenediaminedisuccinic acid of the formula (1) by (a) Precultivation of a strain of the genus Amycolatopsis on a specified nutrient medium (1st preculture), (b) Inoculation of a nutrient solution of the same composition as the base of the production fermenter by the 1st preculture (2nd preculture), (c) Inoculation of the base nutrient solution in the production fermenter with the 2nd preculture and incubation in accordance with a specified timetable, (d) Feeding of the production fermenter in the fed-batch process with a feeding solution under aerobic conditions at a pH of from 2 to 8 and at a temperature of from 15° to 40° C., wherein the base nutrient and feeding solutions are free of zinc-containing compounds.

It is possible to use for the precultivation of the strain of Amycolatopsis (1st preculture) used according to the invention either a synthetic or a natural medium which comprises the nutrients necessary for growth of the microorganisms. For the purpose of the present invention, the precultivation is carried out in an aqueous nutrient medium which comprises as carbon source a carbohydrate such as, for example, glucose, galactose, sucrose, soya flour etc, or preferably polyols such as, for example, glycerol, mannitol, etc. or else a mixture of carbohydrates and polyols.

Examples of suitable nitrogen sources are ammonium hydrogen phosphate, aspartate, glutamate or, where appropriate, urea. Ammonium hydrogen phosphate is preferably used as nitrogen source.

It is furthermore possible to add to the medium inorganic compounds such as, for example, dipotassium hydrogen, potassium dihydrogen, disodium hydrogen or sodium dihydrogen phosphate, magnesium sulphate, magnesium chloride, calcium chloride, sodium chloride, potassium chloride, calcium nitrate or magnesium nitrate etc.

The precultivation is normally carried out as shake culture in a conical flask, for example in a 500 ml conical flask with a septum arm on the side and containing 100 ml of nutrient solution. Such a nutrient solution comprises, for example, 2% full-fat soya flour, 2% glycerol and deionized water. The incubation is carried out, for example, at temperatures of from 15° to 40°, preferably 25° to 30° C., for 24 to 72, preferably 42 to 50 hours. The employed strains grow well on this nutrient solution but produce no EDDS.

A 2nd preculture is then inoculated with about 5 parts (based on the volume of the 2nd preculture) on a nutrient medium which corresponds to the later production medium in the fermenter. Subsequently, the production fermenter is inoculated with part of this 2nd preculture (about 5%). In this way, the original content of the nutrient medium falls to below 0.05 g/l in the production fermenter, which has very beneficial effects on the later working up.

The subsequent fermentation normally takes place in agitated and aerated or otherwise mixed fermenters at a temperature of, for example, from 15° to 40°, preferably 25° to 30° C. and at a pH of, for example, from 3 to 8 at the start of the cultivation. It has emerged that the aeration is not a critical parameter for the present process. However, a minimum oxygen supply is necessary.

The base nutrient solution in the fermenter preferably consists essentially of glycerol and zinc-free inorganic salts such as, for example, magnesium sulphate, potassium dihydrogen phosphate, ammonium hydrogen phosphate, acetic acid and iron(II) citrate. The compounds forming the base nutrient solution are sterilised separately before use in the fermenter.

A typical nutrient solution for the process according to the invention has, for example, the following composition:

10 to 50, preferably 15 to 30 g/l glycerol,
0.5 to 5, preferably 1 to 2 g/l $MgSO_4$ 7 $H_2O$,
7.5 to 20, preferably 10 to 15 g/l $KH_2PO_4$,
0.5 to 20, preferably 1 to 10 g/l $(NH_4)_2HPO_4$,
0.1 to 5, preferably 0.5 to 2 g/l acetic acid, and
25 to 100, preferably 40 to 80 mg/l Fe(III) citrate.

The main culture is cultivated in a batch process until a C limitation is evident from the $pO_2$ curve. The feeding must be started (fed-batch process) no later than this time (about 48 hours).

The feeding of the fermenter usually takes place with a carbon-containing compound, preferably using glycerol or a mixture of glycerol, glutamic acid and magnesium sulphate. The feeding usually takes place at a static pH of from 3 to 8, preferably 6.5 to 8. The pH is adjusted with ammonium sulphate and sulphuric acid on feeding with glycerol alone, and the pH is adjusted with sodium hydroxide and sulphuric acid on feeding of a mixture of glycerol, glutamic acid and magnesium sulphate.

In the process according to the invention under zinc deficiency conditions in the fed-batch process, that is to say with feeding with glycerol alone, yields of about 4 to 5 g/l of culture are obtained after a feeding time of 72 hours. The yields can be increased further on feeding with a glycerol/glutamic acid mixture. It is possible with this mixture, when glycerol and glutamic acid are used in the molar ratio of from 31:1 to 4:1, to obtain 10 g/l product after a feeding time of 155 hours.

In a prior art process, that is to say in a pure batch fermentation with a base nutrient solution, by contrast, yields of only about 1 to 1.5 g/l are obtained.

To work up the culture after the fermentation is complete, it is filtered, where appropriate with the addition of a filtration aid such as, for example, Hyflo. The culture filtrate is then adjusted, for example with hydrochloric acid, to a strongly acidic pH, for example of from 1.5 to 2, cooled and stored at about 4° C. for about 8 to 12 hours. The (S,S)-EDDS which has crystallised out is filtered off and then recrystallised. The resulting crude product comprises more than 90% (S,S)-EDDS. Further EDDS is obtained from the filter residue. The combined crude products are then recrystallised, preferably from hot deionized water, and cooled. The resulting product usually comprises more than 90% (S,S)-EDDS.

The (S,S)-EDDS prepared according to the invention is used as complexing agent, preferably in household detergents. The complexing agent used in detergents has the task of preventing, by forming water-soluble complexes, precipitates of alkaline earth metal salts, preferably calcium and magnesium salts, which are produced during the washing process and become attached to the laundry and machines as troublesome deposits and may accumulate after several washing processes. Conditions are particularly unfavourable when the complexing agent is present in a substoichiometric ratio relative to multiply charged metal ions, for example during the rinsing process. The result then is mainly precipitation of carbonates and insoluble salts of the complexing agents with the hardness elements in the water. The result may then be that larger crystals grow, due to crystallisation seeds, on textiles or washing machine components. The (S,S)-EDDS prepared according to the invention which, like EDTA, forms a chelate complex with the corresponding metal ion is able to prevent the precipitation of insoluble salts even when substoichiometric amounts of complexing agents are used, or may at least have the effect that the insoluble salts are produced in amorphous form, and the formation of sharp-edged, fibre-damaging crystals (for example calcite crystals) is substantially suppressed.

The following examples serve to illustrate the invention.

PREPARATION EXAMPLES

Example 1

The following producer strains are used for the microbiological preparation of (S,S)-EDDS:

1. *Amycolatopsis orientalis,* strain No. MG 417-CF17 in the collection of the Institute of Microbial Chemistry, Tokyo;

2. *Amycolatopsis orientalis* ssp. lurida, Deutsche Sammlung von Mikroorganismen No. 43134; the strain was originally described as ristocetin producer;

3. *Amycolatopsis orientalis,* ssp. lurida, Strain No. 7654 of the IMET (=external section of the DSM, Jena)

The seed material is cultivated in two precultures.

1st Preculture

Cultivation takes place as shake culture in a 500 ml conical flask with a septum arm on the side and 100 ml of nutrient solution of the following composition:

2% full-fat soya flour;
2% glycerol, and
deionized water, ad 100%.
Incubation takes place at a temperature of 27° C. for 48 hours.

The strains grow well on this nutrient solution but produce no EDDS.

2nd Preculture

A 2nd preculture is inoculated with 5% of the 1st preculture on the production medium. Incubation takes place at a temperature of 27° C. for 48 hours. The production medium has the following composition:

25 g/l glycerol,
1.2 g/l $MgSO_4$ 7 $H_2O$,
13.3 g/l $KH_2PO_4$,
4.0 g/l $(NH_4)_2HPO_4$,
1.7 g/l citric acid,
60 mg/l Fe(III) citrate, and
deionized water, ad 100%.

Glycerol and $MgSO_4$ 7 $H_2O$ are sterilised separately. The nutrient solution is sterilised at 121° C. for 30 minutes.

A 2nd preculture is then inoculated with about 5 parts (based on the volume of the 2nd preculture) on a nutrient medium which corresponds to the later production medium in the fermenter. The production fermenter is then inoculated with one part of this 2nd preculture (about 5%). In this way, the original content of 20 g/l soya flour in the first shake culture falls to below 0.05 g/l in the production fermenter, which has very beneficial effects on the later working up.

Cultivation takes place in a batch process until a C limitation is evident from the $pO_2$ curve. The feeding is started no later than this time (about 48 hours).

The fermentation is carried out in a fed-batch process in a commercial 5 l fermenter. Incubation takes place at a static pH of 6.8. An aqueous 88.5% strength glycerol solution is used as feeding solution. The pH is adjusted with $NH_4OH$ and $H_2SO_4$. Strict care is moreover taken that the feeding solution is free as far as possible of zinc-containing compounds, that is to say the concentration of $Zn^{2+-}$ ions must not exceed 2 $\mu$mol/l.

The partial pressure of oxygen is regulated at $pO_2 \geq 10\%$ from the start of feeding. The feeding rate is 12 ml/h feeding solution. After a feeding time of 72 hours, 4.3 to 4.8 g/l EDDS are obtained.

The working up is carried out in the following way: the culture obtained (pH 6.8 to 7.0) is filtered with the addition of 2% Hyflo Super-Cel. The culture filtrate is adjusted with hydrochloric acid to pH 1.5 to 1.8, cooled and stored at 4° C. for 8 to 12 hours. The (S,S)-EDDS which has crystallised out is filtered off and then recrystallised. The resulting crude product contains more than 90% EDDS. The filter residue is washed with cold, very dilute hydrochloric acid (0.01N), then adjusted to pH 8 with 5N NaOH while stirring, and filtered, and the filtrate is again adjusted to a pH 1.5 with concentrated hydrochloric acid, whereupon the EDDS precipitates. For recrystallisation, the crude products are dissolved in hot deionized water and then slowly cooled to 4° C. The resulting product contains more than 90% (S,S)-EDDS.

Example 2

The process is carried out as described in Example 1 but with the difference that, in place of glycerol alone, the feeding solution used is a mixture of glycerol, glutamic acid and $MgSO_4$, which is prepared in the following way:

water is added to
888 g 88.5% pure glycerol and
64 g $MgSO_4$ 7 $H_2O$
and the mixture is sterilised in an autoclave.
465 g of sodium glutamate are dissolved in
3077 ml of deionized water and sterilised separately.
The two sterile solutions are then combined.

Once again, strict care is taken that the feeding solution is as free as possible of zinc-containing compounds, that is to say the concentration of $Zn^{2+-}$ ions must not exceed 2 μmol/l.

The pH of 6.8 is adjusted with 5N sodium hydroxide solution and 5N $H_2SO_4$.

the feeding rate is 12 ml/h feeding solution. After a feeding time of 155 hours, 10 g/l EDDS are obtained.

Determination of (S,S)-EDDS by HPLC (S,S)-EDDS is determined as $Cu^{2+}$ complex by ion-pair HPLC.
Column used: Shandon ODS Hypersil (5 μm) 125×4.6 mm, I.D., with 20×4.6 mm I.D. precolumn with the same packing.
Eluent:
(A) 10 mM sodium phosphate puffer (pH 7.2) with 5 mM TBA
(B) Acetonitrile
Gradient:

| Time (min) | A(%) | B(%) |
|---|---|---|
| 0 | 96 | 4 |
| 5 | 96 | 4 |
| 6 | 40 | 60 |
| 7 | 40 | 60 |
| 8 | 96 | 4 |
| 13 | 96 | 4 |

Flow rate: 2 ml/min
Detection: 253 nm

Sample preparation: The culture broth is centrifuged, and diluted where appropriate. 1 ml is mixed with 20 μl of a 100 mM $CuSO_4$ solution and centrifuged again. The supernatant is used for the analysis.
Volume injected: 20 μl

What is claimed is:

1. A process for the preparation of N,N'-ethylenediaminedisuccinic acid of the formula

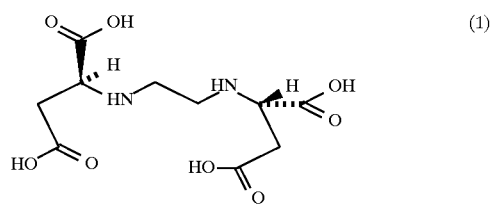

by
(a) Precultivation of a strain of the genus *Amycolatopsis orientalis* on a specified nutrient medium (1st preculture),
(b) Inoculation of a nutrient solution of the same composition as the base of the production fermenter by the 1st preculture (2nd preculture),
(c) Inoculation of the base nutrient solution in the production fermenter with the 2nd preculture and incubation in accordance with a specified timetable,
(d) Feeding of the production fermenter in the fed-batch process with a feeding solution under aerobic conditions at a pH of from 2 to 8 and at a temperature of from 15° to 40° C.,
wherein the base nutrient and feeding solutions are free of zinc-containing compounds.

2. A process according to claim 1, wherein the base nutrient solution comprises glycerol as main constituent.

3. A process according to claim 1, wherein the base nutrient solution consists of
10 to 50 g/l glycerol,
0.5 to 5 g/l $MgSO_4$ 7 $H_2O$,
7.5 to 20 g/l $KH_2PO_4$,
0.5 to 20 g/l $(NH_4)_2HPO_4$,
0.1 to 5 g/l citric acid, and
25 to 100 mg/l Fe(III) citrate.

4. A process according to claim 1, wherein the feeding solution consists of
(a) glycerol or of
(b) a mixture of glycerol, glutamic acid and $MgSO_4$.

5. A process according to any of claims 1 to 4, wherein the fed-batch process is carried out at constant pH.

* * * * *